United States Patent [19]

Greenhouse et al.

[11] Patent Number: 4,654,360
[45] Date of Patent: Mar. 31, 1987

[54] 1,2,3-TRISUBSTITUTED INDOLES FOR TREATMENT OF INFLAMMATION

[75] Inventors: Robert J. Greenhouse, Coyoacan, Mexico; Joseph M. Muchowski, Sunnyvale, Calif.

[73] Assignee: Syntex (U.S.A.) Inc., Palo Alto, Calif.

[21] Appl. No.: 616,346

[22] Filed: Jun. 1, 1984

[51] Int. Cl.$^4$ .................. C07D 209/30; C07D 209/40; A61K 31/40
[52] U.S. Cl. .................................... 514/418; 548/483; 548/484; 548/485; 548/486
[58] Field of Search ............... 548/484, 485, 486, 483; 514/418

[56] References Cited

U.S. PATENT DOCUMENTS

| | | | |
|---|---|---|---|
| 3,441,570 | 4/1969 | Meyer | 548/486 |
| 3,489,770 | 1/1970 | Herbst | 548/504 |
| 3,665,016 | 5/1972 | Bourdais | 548/486 |
| 3,860,609 | 1/1975 | Lundt | 548/484 |
| 4,428,962 | 1/1984 | Bristol et al. | 548/483 |

OTHER PUBLICATIONS

Tomita et al., "The Reaction of Indoles with Succinimido–Sulfonium Salts . . . ", *Chem. Abst.* 85:46294(1976).
Nagarathnam et al., "1 Benzenesulfonyl-2-Bromomethyl-3-phenylthio Indole . . . ", *Chem. Abst.* 101:54848e (1984).
Nagarathnam et al., "1 Benzenesulfonyl-2-Bromomethyl-3-Phenylthio Indole," *Chem. Abst.* 98:197932, (1983).
Noller, Carl, *Textbook of Organic Chemistry*, W. B. Saunders, Philadelphia (1966), p. 258.

*Primary Examiner*—Glenna M. Hendricks
*Attorney, Agent, or Firm*—Liza K. Toth; Tom M. Moran

[57] ABSTRACT

Disclosed are compounds of the formula

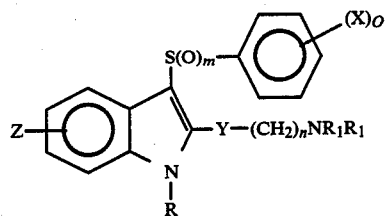

wherein the several groups are defined herein. These compounds are useful for treating inflammation.

26 Claims, No Drawings

1,2,3-TRISUBSTITUTED INDOLES FOR TREATMENT OF INFLAMMATION

BACKGROUND OF THE INVENTION

This invention relates to 1,2,3-substituted indoles which are useful as lipoxygenase inhibitors. More specifically, this invention relates to indoles wherein the nitrogen is substituted by an alkyl or benzyl group, the 2-position is substituted by the group —Y—$(CH_2)_n NH_2$, and position 3 has an —$S(O)_m$aryl group.

These compounds are useful for treating inflammation as they are inhibitors of human polymorphonuclear leukocyte lipoxygenase. This lipoxygenase catalyzes the hydroperoxidation of polyunsaturated fatty acids, esters, alcohols, etc., containing a cis-cis-1,4-pentadiene system. The product is a 1-hydroperoxy-2,4-trans,cis-pentadiene-containing molecule.

Of particular interest is the conversion of arachidonic acid to leukotrienes. Leukotrienes, earlier known as slow reacting substance of anaphylaxis, are known to be involved in inflammation and anaphylaxis. The compounds of this invention are useful for treating inflammation, asthma, diverse allergic states, adult respiratory distress syndrome, psoriasis, gout, etc., as they inhibit the lipoxygenase enzyme responsible for conversion of arachidonic acid to leukotrienes from arachidonic acid by the lipoxygenase route.

SUMMARY OF THE INVENTION

The novel compounds of this invention are those represented by formula I

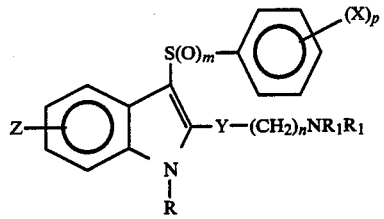

wherein
R is alkyl of 1 to 8 carbon atoms, benzyl or benzyl substituted with one or more groups independently selected from the group alkyl of 1 to 4 carbon atoms, halo, —$OR_2$ where $R_2$ is alkyl of 1 to 4 carbon atoms, —$OCF_3$, —$SO_2CH_3$, —$CO_2H$, —$CO_2R_2$, —CHO, —$NO_2$, —$CF_3$, —SCN, —$OCH_2O$—;
$R_1$ is hydrogen or alkyl of 1 to 4 carbon atoms;
Y is S, NH, or $NR_2$;
n is 2–8;
m is 0,1 or 2;
X and Z are independently alkyl of 1 to 4 carbon atoms, halo, —$OR_2$ where $R_2$ is alkyl of 1 to 4 carbon atoms, —$OCF_3$, —$SO_2CH_3$, —$CO_2H$, —$CO_2R_2$, —CHO, —$NO_2$, —$CF_3$ or —SCN;
p is 0, 1, 2, 3, 4, or 5; and the pharmaceutically acceptable salts thereof.

In a second aspect, this invention relates to a method for treating inflammation which method comprises administering to a subject a therapeutically effective amount of a compound of formula I either alone or in admixture with a pharmaceutically acceptable excipient wherein formula I wherein
R is alkyl of 1 to 8 carbon atoms, benzyl or benzyl substituted with one or more groups independently selected from the group alkyl of 1 to 4 carbon atoms, halo, —$OR_2$ where $R_2$ is alkyl of 1 to 4 carbon atoms, —$OCF_3$, —$SO_2CH_3$, —$CO_2H$, —$CO_2R_2$, —CHO, —$NO_2$, —$CF_3$, —SCN, —$OCH_2O$;
$R_1$ is hydrogen or alkyl of 1 to 4 carbon atoms;
Y is S, NH, $NR_2$, or;
n is 2–8;
m is 0,1 or 2;
X and Z are independently alkyl of 1 to 4 carbon atoms, halo, —$OR_2$ where $R_2$ is alkyl of 1 to 4 carbon atoms, —$OCF_3$, —$SO_2CH_3$, —$CO_2H$, —$CO_2R_2$, —CHO, —$NO_2$, —$CF_3$ or —SCN;
p is 0, 1, 2, 3, 4, or 5; and the pharmaceutically acceptable salts thereof.

DETAILED DESCRIPTION

The preferred compounds of this invention are those wherein Y is S. More preferred are those compounds wherein R is benzyl or substituted benzyl, Y is S, n is 2, m is 2, X is halo, alkyl of 1 to 4 carbon atoms; —$OR_2$ or —$COOR_2$, o is 1 and Z is hydrogen.

Most preferred are the compounds:
1-benzyl-2-aminoethylthio-3-phenylsulfonylindole;
1-(2-methoxycarbonylbenzyl)-2-aminoethylthio-3-phenylsulfonylindole;
1-(4-chlorobenzyl)-2-aminoethylthio-3-phenylsulfonylindole;
1-(-4-methylbenzyl)-2-aminoethylthio-3-phenylsulfonylindole;
1-benzyl-2-aminoethylthio-3-(4-methylphenylsulfonyl)indole; and
1-benzyl-2-aminoethylthio-3-(4-chlorophenylsulfonyl)indole.

DEFINITIONS

"Pharmaceutically acceptable salt" refers to those salts which retain the biological effectiveness and properties of the free base or free acid, which ever may be the case, and which are not biologically or otherwise undesirable.

Acid addition salts may be formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like.

The compounds of formula I in free base form may be converted to the acid addition salts by treating with a stoichiometric excess of the appropriate organic or inorganic acid. Typically, the free base is dissolved in an organic solvent such as ether, ethanol or methanol, and the acid added thereto. The temperature is maintained between about 0° C. and 100° C. The resulting acid addition salt precipitates spontaneously or may be brought out of solution with a less polar solvent.

The acid addition salts of the compounds of formula I may be decomposed to the corresponding free base by treating with a stoichiometric excess of a suitable base, such as potassium carbonate or sodium hydroxide, typically in the presence of aqueous solvent, and at a temperature of between about 0° C. and 100° C. The free base from is isolated by conventional means, such as extraction with an organic solvent.

Salts of the compounds of formula I may be interchanged by taking advantage of differential solubilities of the salts, volatilities or acidities of the acids, or by treating with the appropriately loaded ion exchange resin. For example, the interchange is effected by the reaction of a salt of the compounds of formula I with a slight stoichiometric excess of an acid of a lower pKa than the acid component of the starting salt. This conversion is carried out at a temperature between about 0° C. and the boiling point of the solvent being used as the medium for the procedure.

When there is a —COOH group in the molecule, for example when R is benzyl substituted with a —COOH group, this function may be converted to a salt with any inorganic or organic base which gives a pharmaceutically acceptable salt. Salts derived from inorganic bases include sodium, potassium, lithium, ammonium, calcium, magnesium, ferrous, zinc, copper, manganous, aluminum, ferric, manganic salts and the like. Particularly preferred are the ammonium, potassium, sodium, calcium and magnesium salts. Salts derived from pharmaceutically acceptable organic non-toxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, tromethamine, dicyclohexylamine, lysine, arginine, histidine, caffeine, procaine, hydrabramine, choline, betaine, ethylenediamine, glucosamine, methylglucamine, theobromine, purines, piperazine, piperidine, N-ethylpiperidine, polyamine resins and the like. Particularly preferred organic non-toxic bases are isopropylamine, diethylamine, ethanolamine, tromethamine, dicyclohexylamine, choline and caffeine.

FORMULATIONS

Administration of the active compounds and salts described herein can be via any of the accepted modes of administration for agents which are antiinflammatory agents.

For solid compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences,* Mack Publishing Company, Easton, Pa., 18th Edition, 1975. The composition or formulation to be administered will, in any event, contain a quantity of the active compound(s) in an amount effective to alleviate the symptoms of the subject being treated.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 10%–95% active ingredient, preferably 25–70%.

For systemic administration via suppository, traditional binders and carriers include, e.g. polyalkalene glycols or triglycerides. Such suppositories may be formed from mixtures containing active ingredient in the range of 0.5%–10%; preferably 1–2%.

SYNTHESIS AND SPECIFIC EMBODIMENTS

The compounds of this invention may be prepared by several methods illustrated by the following reaction schemes.

Reaction Scheme I

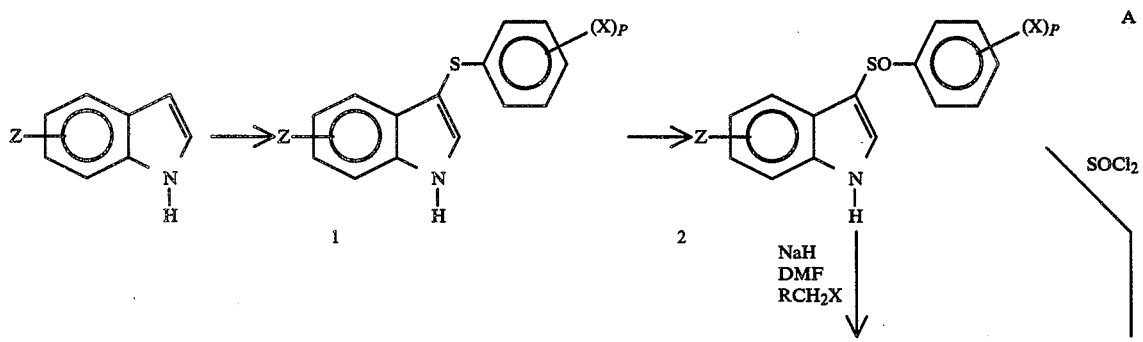

4,654,360
-continued
Reaction Scheme I
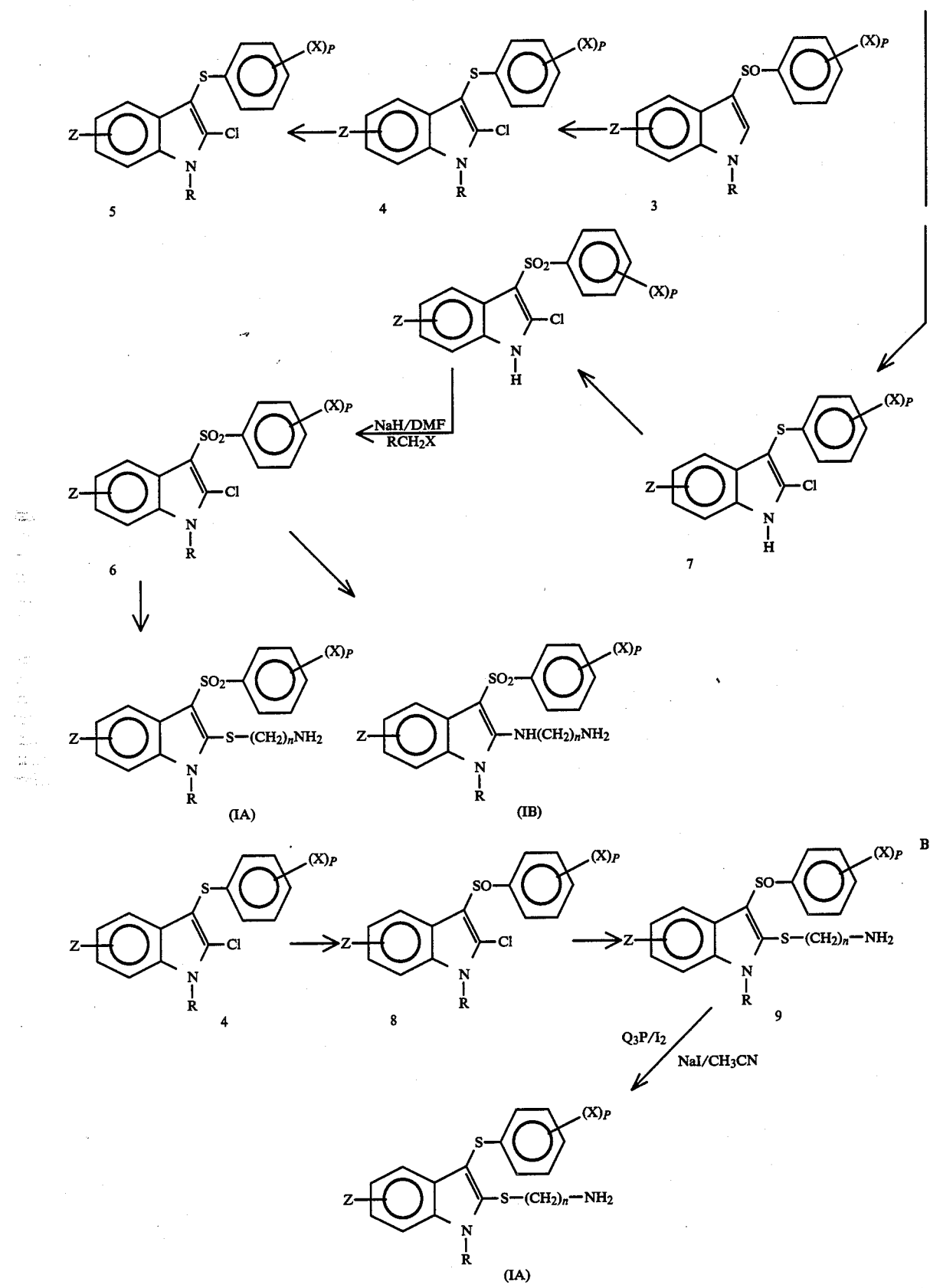

Reaction Scheme II

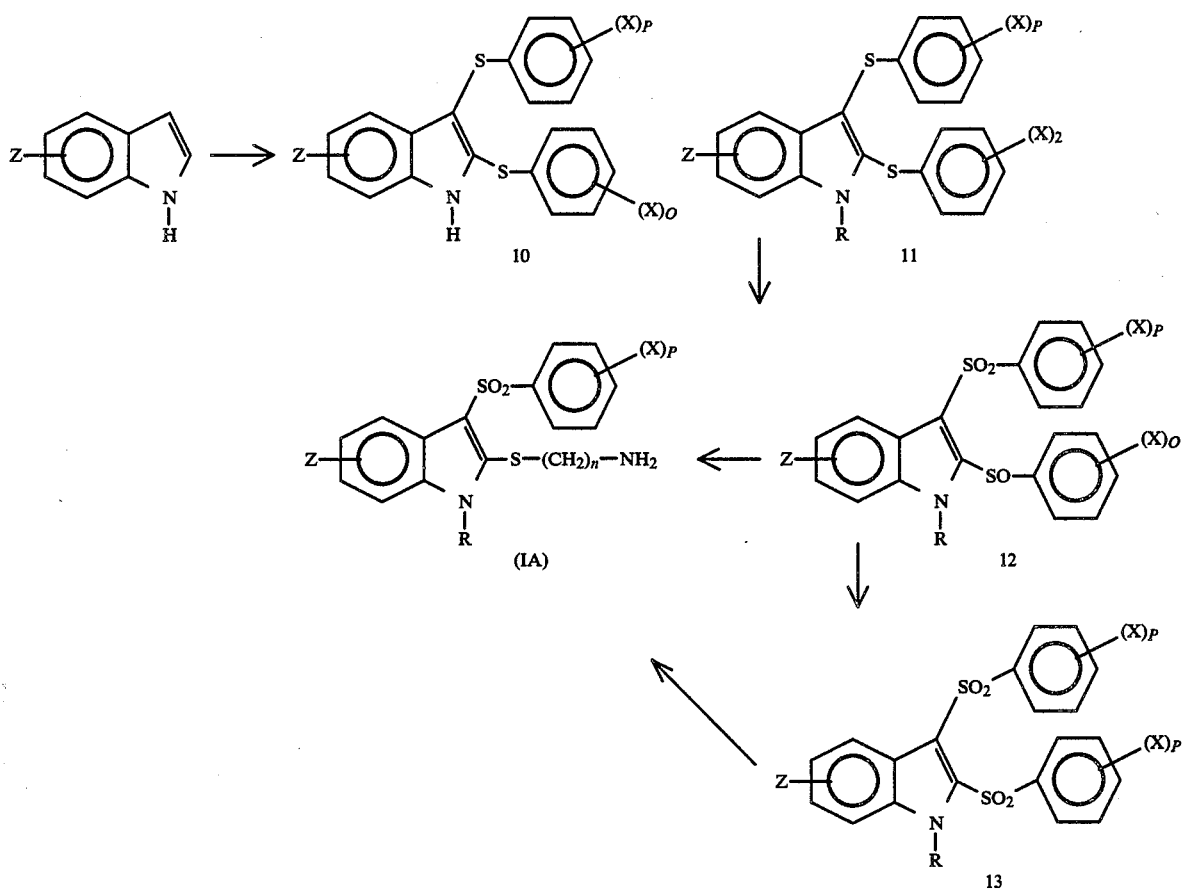

A general starting point is to begin with indole, a commercially available compound, and then substitute position 3 and 1, then position 2 to obtain the free amine.

EXAMPLE 1

3-Phenylthioindole

This compound was prepared according to the method described by K. Anzai, *J. Heterocycl. Chem.*, (1979), 16, 567.

EXAMPLE 2

3-Methylthioindole

This compound was prepared according to the method described by K. Tomita, et. al. *Heterocycles*, (1976), 4, 729 or P. G. Gassman, et. al. *J. Am. Chem. Soc.*, (1973), 95, 59.

EXAMPLE 3

3-(4-Chlorophenylthio)indole

This compound was prepared according to method of Anzai (see Example 1). M.P.-138°–139° C. (hexane-dichloromethane); U.V.-221, 260, 279, 289, 309 sh nm ($\epsilon$ 26,300; 17,000; 11,200; 8320; 1072).

EXAMPLE 4

3-Phenylsulfinylindole

Solid m-chloroperbenzoic acid (1.93 g, 9.77 mmol) was added in small portions to a well stirred solution of 3-phenylthioindole (2.0 g, 8.88 mmol) in dry dichloromethane (100 ml) at 0°. Five min after the addition was terminated, the reaction was completed. The solution was washed with saturated sodium bicarbonate solution, the organic phase diluted with ether, dried over sodium sulfate and evaporated in vacuo. The residue was crystallized from ether-hexane to give the title compound, M.P.-126°–127° C.

Proceding in the same manner, there was also made 3-(4-Chlorophenylsulfinyl)indole: M.P.-129.5°–130.5° dec (ether-dichloromethane); U.V.-239, 269, 276, 285 nm ($\epsilon$ 13,200; 10,000; 9120; 7080).

EXAMPLE 5

3-Methylsulfinylindole

Potassium persulfate (KHSO$_5$, 55 g, 179 mmol) in water (300 ml) was slowly added to a solution of 3-methylthioindole (29.3 g, 179 mmol) in methanol (300 ml) cooled in a ice bath. One half hour after the addition was completed, water was added, the solution was saturated with sodium chloride and the product was extracted into chloroform. The extract was dried, evaporated in vacuo and the residue was crystallized from chloroform-ethyl acetate to give the title product.

M.P.-134°–135° C.; U.V.-213, 267, 276 sh, 284 nm ($\epsilon$ 52,500; 11,000; 10,500; 7940).

EXAMPLE 6

3-(4-Methylphenylsulfinyl)indole

Toluenesulfinyl chloride was prepared according to Org. Syn., IV, 937 on half the scale described (that is, on 0.1 mole sodium toluenesulfinate). The crude sulfinyl chloride (15.2 g) was added dropwise to 11 g of indole dissolved in dichloromethane (200 ml) at 0° C. in the presence of 20 g of sodium bicarbonate. After 30 min at room temperature, the reaction mixture was washed well with saturated sodium bicarbonate solution, the phases separated and the organic phase dried and evaporated. The crude material was applied to a short silica gel column. Elution with dichloromethane removed a large amount of non-polar material. The product was removed with ethyl acetate. Upon recrystallization from ethyl acetate, the compound had melting point 120.5–121.5 (dec.) (corr.).

EXAMPLE 7

1-Methyl-3-phenylsulfinylindole

Sodium hydride in mineral oil (60% suspension, 0.036 g, 0.90 mmol) was suspended in dry dimethylformamide (10 ml) and a solution of 3-phenylsulfinylindole (0.200 g, 0.82 mmol) in dry dimethylformamide (10 ml) was added dropwise thereto with stirring. After 0.5 hours at room temperature, methyl iodide (0.057 ml) was added and fifteen minutes thereafter the mixture was diluted with water. The product was extracted into benzene, the extract dried and evaporated in vacuo. Crystallization of the residue from ethyl acetate-ether gave the title compound as a solid.

M.P.-120° C.; U.V.-223, 280 nm ($\epsilon$ 22,400; 9330).

EXAMPLE 8

1-Benzyl-3-phenylsulfinylindole

This compound was prepared in the same manner as described in Example 7 using sodium hydride (0.036 g, 50% in mineral oil; 0.90 mmol), dimethylformamide (5 ml), 3-phenylsulfinylindole (0.200 g, 0.82 mmol) and benzyl bromide (0.11 ml, 0.154 g, 0.90 mmol). Crystallization of the crude product from dichloromethane-hexane gave the title compound. M.P.-148°–149° (dichloromethane-hexane).

U.V.-225, 279 nm ($\epsilon$ 23,400; 10,200).

Proceding in the same manner, the following compounds were prepared:
1-Benzyl-3-(4-chlorophenylsulfinyl)indole)
M.P. 138°–138.5° dec (ether-dichloromethane)
U.V. 230, 284 sh, 291 nm ($\epsilon$ 14,800; 11,700; 12,000).
1-Benzyl-3-(4-methylphenylsulfinyl)indole,
M.P. 127.5–128.5 (ethyl acetate-hexane).

EXAMPLE 9

1-Benzyl-3-phenylsulfinylindole

A mixture of toluene (100 ml), 50% sodium hydroxide (20 ml), 3-phenylsulfinylindole (4.27 g, 17.7 mmol) and benzyltrimethylammonium chloride (6.01 g, 26.5 mmol) was vigorously stirred at reflux temperature for 4 hours. The organic phase was separated and combined with an ether extract of the aqueous phase. The extract was dried and evaporated in vacuo giving a solid which on crystallization from dichloromethane-hexane gave the solid product. Chromatography of the mother liquor on silica gel using hexane-ethyl acetate (3:2) as the eluant gave a further quantity of the title compound, m.p. 148°–149° C. identical to the material prepared in Example 8.

EXAMPLE 10

1-Benzyl-3-methylsulfinylindole

Solid 3-methylsufinylindole (0.20 g, 1.12 mmol) was added to a stirred suspension of sodium hydride (0.058 g, 50% in mineral oil; 1.22 mmol) in dry dimethylformamide (20 ml). After 5 min benzyl bromide (0.13 ml, 0.188 g, 1.1 mmol) was added and after 0.5 h water was added to the reaction mixture and the product was extracted into dichloromethane. The extract was dried and evaporated to give a residue which was subjected to tlc on silica gel using ethyl acetate as the developing solvent. This procedure gave a solid which was crystallized from dichloromethane-hexane.

M.P.-110°–111° (dichloromethane-hexane).
U.V.-215, 273 nm ($\epsilon$ 38,000; 8910).

EXAMPLE 11

1-Benzyl-2-chloro-3-phenylthioindole

A solution of thionyl chloride (0.03 ml, 0.054 g, 0.45 mmol) in dry dichloromethane (5 ml) was added dropwise to a stirred solution of 1-benzyl-3-phenylsulfinylindole (0.150 g, 0.45 mmol) in dry dichloromethane (20 ml), containing suspended sodium bicarbonate (1 g), maintained at 0° C. One half hour after the addition was completed the reaction was quenched with a saturated solution of aqueous sodium bicarbonate. The organic phase was separated, combined with a dichloromethane extract of the aqueous phase and the combined organic phases were dried and evaporated in vacuo. Crystallization of the residue from dichloromethane/hexane gave the title product.

M.P.-107°–108° (dicholoromethane-hexane).
U.V.-222, 247, 283, 291 nm ($\epsilon$ 36,300; 17,000; 11,200; 10,700).

Proceeding in the same manner, there was made:
1-benzyl-2-chloro-3-methylthioindole
M.P.-48°–49° (ether-pentane).
U.V.-217, 225 sh, 281, 290 nm ($\epsilon$ 35,500; 8910; 9770; 8710).
1-methyl-2-chloro-3-phenylthioindole,
M.P.-85°–86° (dichloromethane-ether).
U.V.-224, 246, 284, 291 nm ($\epsilon$ 36,300; 17,800; 11,700, 10,500).
1-benzyl-2-chloro-3-(4-chlorophenylthio)indole,
M.P.-90.5°–91.5° (hexane-dichloromethane);
1-benzyl-2-chloro-3-(4-methylphenylthio)indole,
M.P.-83°–84° (ether-hexane).
U.V.-233, 248, 284, 292 nm ($\epsilon$ 16,600; 16,200; 11,800; 10,200).

EXAMPLE 12

2-Chloro-3-phenylthioindole

Thionyl chloride (0.19 ml, 0.31 g, 2.7 mmol) in dry dichloromethane (9 ml) was added dropwise to a stirred solution of 3-phenylsulfinylindole (0.618 g, 2.74 mmol) in dry dichloromethane (40 ml) containing suspended sodium bicarbonate (2 g, 23 mmol) at 0°. Five minutes after termination of the addition the reaction mixture was washed with saturated sodium bicarbonate solution, the organic phase was dried and evaporated in vacuo. The residue was subjected to thin layer chromatography on silica gel using hexane-ethyl acetate (4:1) to elute the product.

M.P.-98°-99° (dichloromethane-pentane).
U.V.-224, 249 sh, 282, 289 nm (ε 30,200; 15,800; 11,200; 9120).

EXAMPLE 13

2-Chloro-3-phenylthioindole

Sulfuryl chloride (0.07 ml, 0.119 g, 0.88 mmol) was added dropwise at 0° to a stirred solution of 3-phenylthioindole (0.200 g, 0.88 mmol) in dry dichloromethane (20 ml). After 1 h the reaction mixture was washed with saturated sodium bicarbonate solution, the organic phase was dried and evaporated in vacuo. The residue was subjected to thin layer chromatography on silica gel eluting the product with hexane-ethyl acetate (7:3). There was obtained the desired product which had m.p. 98°-99° after crystallization from dichloromethane-pentane, and was identical to the material prepared in Example 13.

EXAMPLE 14

1-Benzyl-2-chloro-3-phenylsulfonylindole

Solid m-chloroperbenzoic acid (2.77 g) was added to a stirred solution of the chloro sulfide 1-benzyl-2-chloro-3-phenylthioindole (2.0 g, 5.71 mmol) in anhydrous dichloromethane (50 ml) at 0°. The cooling bath was removed and after 10 min the solution was washed with saturated sodium bicarbonate solution. The organic phase was dried, evaporated in vacuo and the residue was crystallized from dichloromethane-hexane to give the title compound.
M.P.-190°-191° (dichloromethane-hexane).
U.V.-219, 288 nm (ε 34,700; 26,900).

Using this procedure, the following compounds were prepared:
1-Benzyl-2-chloro-3-(4-chlorophenylsulfonyl)indole
M.P.-155°-155.5° (ether).
U.V.-220, 235 sh, 284, 290 nm (ε 24,500; 20,400; 14,100; 14,100).
1-Benzyl-2-chloro-3-(4-methylphenylsulfonyl)indole
M.P.-172°-174° (ether-dichloromethane).
U.V.-233, 288 nm (ε 14,100; 12,600).

EXAMPLE 15

1-Benzyl-2-chloro-3-methylsulfonylindole

This compound was prepared from the sufide (0.200 g, 0.695 Mmol) 1-benzyl-2-chloro-3-methylthioindole in the same manner as described in Example 14 using m-chloroperbenzoic acid (0.298 g, 1.39 mmol) in dichloromethane (40 ml).
M.P.-158°-159° (dichloromethane-hexane).
U.V.-213, 272, 279, 287 nm (ε 18,200; 20,900; 21,900; 18,200).

EXAMPLE 16

2-Chloro-3-phenylsulfonylindole

A solution of m-chloroperbenzoic acid (80%, 13.9 g) in dry dichloromethane (100 ml) was added with stirring, at 0°, to a solution of 2-chloro-3-phenylthioindole (7.6 g, 29.3 mmol) in dry dichloromethane (200 ml). After 4 h at 0° the reaction mixture was washed with saturated sodium carbonate solution, the organic phase was separated and combined with an ethyl acetate extract of the aqueous phase. The organic phases were dried and evaporated in vacuo giving a solid which was crystallized from ethyl acetate-hexane.
M.P.-197°-198° (ethyl acetate-hexane).
U.V.-225, 281, 288 nm (ε 11,000; 10,800; 10,500).

EXAMPLE 17

1-(4-Methylbenzyl)-2-chloro-3-phenylsulfonylindole

A solution of 2-chloro-3-phenylsulfonylindole (1.5 g, 5.14 mmol) in dry dimethylformamide (10 ml) was added dropwise to a stirred suspension of sodium hydride (0.226 g, 60% in mineral oil) in dry dimethylformamide (15 ml). The mixture was stirred at room temperature for 1.5 hours at the end of which time 4-methylbenzylbromide (1.05 g) was added in one portion. After 2 hours the solution was poured into water, and the product was extracted into ether. The aqueous phase was saturated with salt and then extracted with benzene. The combined extracts were washed with water, dried and evaporated in vacuo. The residue was passed through a short column of silica gel using hexane-ethyl acetate (7:3) to elute the product. The solid product was crystallized from ethyl acetate-hexane to give a white crystalline material.
M.P.-165°-166° (ethyl acetate-hexane).
U.V.-223, 284, 276 sh, 290 nm (ε 23,500; 13,500; 12,300; 13,200).

EXAMPLE 18

1-(4-Chlorobenzyl)-2-chloro-3-phenylsulfonylindole

This compound was prepared in the same manner as described in Example 17 except that following the addition of 4-chlorobenzylchloride to the anion of 2-chloro-3-phenylsulfonylindole, the reaction mixture was stirred at 90° for 4 hours. The crude product was crystallized from dichloromethane-hexane to give the product.
M.P.-187°-188°.
U.V.-228, 227 sh, 284, 291 nm (E 19,500; 12,000; 12,900; 12,600).

EXAMPLE 19

1-Benzyl-2-aminoethylthio-3-phenylsulfonylindole

A solution of 2-aminoethanethiol hydrochloride (0.061 g, 0.52 mmol) in dry dimethylformamide (5 ml) was added dropwise to a stirred suspension of sodium hydride (0.042 g, 60% in mineral oil, 1.04 mmol) in dry dimethylformamide (10 ml) at room temperature. One half hour after the addition was completed, a solution of 5a (0.200 g, 0.52 mmol) in dry dimethylformamide (5 ml) was added and stirring was continued for 4 h. The solution was diluted with water, the product was extracted into ethyl acetate, the extract was dried and evaporated in vacuo at a temperature less than 30°. The residue was crystallized from ethyl acetate-ether to give the product (0.141 g, 69%). Recrystallization from dichloromethane-hexane gave the title compound.
M.P.-150°-151° (dichloromethane-hexane).
U.V.-224, 300 nm (ε 25,100; 15,900).

EXAMPLE 20

1-Benzyl-2-aminoethylthio-3-phenylsulfonylindole

The hydrochloroide of 2-aminoethanethiol (2.56 g) dissolved in dry dimethylformamide (40 ml) was added dropwise, at 0°, to a stirred suspension of sodium hydride (2.0 g, 60% in mineral oil) in dry dimethylformamide (40 ml) maintained in a nitrogen atmosphere. The mixture was stirred for 1.5 hours at room temperature and then there was added the bis sulfone from Example 37 (10.0 g, 20.5 mmol). After 0.5 hours the mixture was diluted with ether, the resulting mixture was washed with water and the organic phase was dried. The solvent was concentrated in vacuo to a volume at which crystallization of the product began to occur. The mixture was cooled and the product was collected by filtration. This material had m.p. 149°–150° and was spectroscopically identical to the material prepared in Example 19.

Using the preceeding procedure, with the appropriate substitution of reactants and converting the crude free base to the hydrobromide salt with ethereal hydrogen bromide the following compounds were made:

1-benzyl-2-aminoethylthio-3-(4-chlorophenylsulfonyl)indole hydrobromide,
M.P.-207° dec (ethyl acetate-methanol).
U.V.-240, 304 nm ($\epsilon$ 13,200; 11,200).

1-benzyl-2-aminoethylthio-3-(4-methylphenylsulfonyl)indole hydrobromide,
M.P.-191°–192° (ethyl acetate-methanol).
U.V.-230, 241, 302 nm ($\epsilon$ 13,200; 13,800; 14,100).

EXAMPLE 21

1-Benzyl-2-aminoethylthio-3-methanesulfonylindole

2-Aminoethanethiol hydrochloride (0.419 g, 3.12 mmol) was added to a stirred suspension of sodium hydride (0.314 g, 50% in mineral oil, 6.56 mmol) in anhydrous dimethylformamide (30 ml) and after 1 hour, 1-benzyl-2-chloro-3-methylsulfonylindole (1.0 g, 3.29 mmol) was added. One half hour thereafter the solution was diluted with water, the product extracted with ether, the extract dried over sodium sulfate and evaporated in vacuo. The product was obtained as a solid, M.P.-95°–96°.

EXAMPLE 22

1-(4-Methylbenzyl)-2-aminoethylthio-3-phenylsulfonylindole

This compound was prepared in the same manner as described for in Example 21 except that the reaction time was 5 hours. The crude product had m.p. 149.5°–150.5°. After crystallization from dichloromethane-ether an analytical specimen was obtained.
M.P.-150°–151° (dichloromethane-ether).
U.V.-222, 229 nm ($\epsilon$ 34,700; 15,200).
I.R.-(CHCl$_3$) 20478.

EXAMPLE 23

1-(4-Chlorobenzyl)-2-aminoethylthio-3-phenylsulfonylindole

This compound was prepared in the same way as given in Example 21 except that the reaction time was 1.5 hours. The product crystallized directly when the ether extract was concentrated to a small volume.
M.P.-149°–150° (ether).
U.V.-226, 300 nm ($\epsilon$ 23,500; 14,800).

EXAMPLE 24

1-(2-Methoxycarbonylbenzyl)-2-aminoethylthio-3-phenylsulfonylindole hydrochloride A solution of 2-aminoethanethiol hydrochloride (0.200 g, 1.76 mmol) in dry dimethylformamide (10 ml) was added, of 0° in a nitrogen atmosphere, to a stirred suspension of sodium hydride (0.155 g, 60% in mineral oil) in dry dimethylformamide (20 ml). After 0.5 hours 1-(2-methoxycarbonylbenzyl)-2-aminoethylthio-3-phenylsulfonylindole (1.0 g) was added and the solution was stirred at room temperature for 2 hours. The solution was diluted with water and the product was extracted with ether. The extract was ried and then evaporated in vacuo, at less than 20°, to a volume of 100 ml. A saturated ether solution of hydrogen chloride gas (5 ml) was added and the mixture was left in the refrigerator for 16 hours. The product was collected by filtration.
M.P.-177° dec. (ether).
U.V.-222, 302 nm ($\epsilon$ 29,500; 14,100).

Proceeding in the same manner, but with the substitution of appropriate starting materials for those recited above the following compound were made:

1-methyl-2-aminoethylthio-3-phenylsulfonylindole hydrobromide
M.P.-130°–135° dec (ethyl acetate)
U.V.-222, 300 nm ($\epsilon$ 29,500; 18,200).

1-Ethyl-2-aminoethylthio-3-phenylsulfonylindole hydrobromide
M.P.-161°–163° (ethyl acetate)
U.V.-224, 300 nm ($\epsilon$ 29,500; 17,800).

EXAMPLE 25

1-(3,4-Methylenedioxybenzyl)-2-aminoethylthio-3-phenylsulfonylindole hydrobromide This compound was prepared in the same manner as described in Example 24 using 1-(3,4-methylenedioxybenzyl)-3-phenylsulfonylindole as the starting material and an ethereal solution of hydrogen bromide gas to prepare the salt. The crude salt was purified by passage through a short column of silica gel using a ethyl acetate-hexane (4:1) to remove non-polar material and then a 1:1 mixture of chloroform and a solution of chloroform-methanol-acetic acid (60:10:1) to elute the solid product. This product was then crystallized from dichloromethane-hexane.
M.P.-185°–186° (dichloromethane-hexane)
U.V.-224, 297 nm ($\epsilon$ 19,500; 16,600).

EXAMPLE 26

1-Benzyl-2-(2-dimethylaminoethylthio)-3-phenylsulfonylindole hydrochloride

A solution of 1-benzyl-2-aminoethylthio-3-phenylsulfonylindole (1.0 g, 2.36 mmol) in 97% formic acid (24 g) containing a 37% formaldehyde solution (aqueous, 0.78 ml) was heated at reflux temperature for 5 hours. The cooled solution was carefully poured into saturated aqueous sodium carbonate solution and the product was extracted into dichloromethane. The extract was dried and excess ethereal hydrogen chloride was added. The solvent was removed in vacuo and the residue was crystallized from dichloromethane-ether to give the title compound.
M.P.-159°–160° (dichloromethane-ether).
U.V.-226, 300 nm ($\epsilon$ 15,900; 13,500).

EXAMPLE 27

1-Benzyl-2-chloro-3-phenylsulfinylindole

A solution of m-chloroperbenzoic acid (8.18 g) in dry dichloromethane (200 ml) was added dropwise to a stirred solution of 1-benzyl-2-chloro-3-phenythioindole (12.09 g) in anhydrous dichloromethane (400 ml). Ten minutes after the addition had been completed the solution was washed with saturated aqueous sodium carbonate solution and dried. The solvent was removed in vacuo to give a solid which was crystallized from acetone-pentane.
M.P.-151°–152° (acetone-pentane).

EXAMPLE 28

1-Benzyl-2-aminoethylthio-3-phenylsulfinylindole hydrochloride

2-Aminoethanthiol hydrochloride (1.74 g, 15 mmol) was added to a stirred suspension of sodium hydride (1.37 g, 50% in mineral oil, 28.5 mmol) in dry dimethylformamide (40 ml). After 2 hours, 1-benzyl-2-chloro-3-phenylsulfinylindole (5.0 g, 13.6 mmol) was added and the solution was stirred for a further 2 hours. The solution was diluted with water which resulted in the deposition of a gummy material. This residue was washed with hexane and then excess ethereal hydrogen chloride was added. The ether was decanted from the solid, the solid was washed with ether by decantation, collected by filtration and dried in vacuo.

M.P.-92°-94° (dichloromethane-pentane).

EXAMPLE 29

2,3-Bisphenylthioindole

This compound was prepared as described by K. Anzai, *J. Heterocycl. Chem.*, (1979), 16, 567.

EXAMPLE 30

1-(2-Methoxycarbonylbenzyl)-2,3-bisphenylthioindole

A solution of 2,3-bisphenylthioindole (3.0 g, 9 mmol) in dry dimethylformamide (10 ml) was added dropwise to a stirred suspension of sodium hydride (0.395 g, 60% in mineral oil) in dry dimethylformamide (10 ml) maintained in a nitrogen atmosphere at room temperature. After 1.5 hours, 2-methoxycarbonylbenzyl bromide (2.26 g, prepared by the method of P. E. Hanna, et al., *J. Med. Chem.*, (1974), 17, 1020) was added and stirring was continued for 3 hours. The solution was diluted with water, the product was extracted into ether, the extract was dried and evaporated in vacuo. The residue was subjected to column chromatography on silca gel using hexane-ethyl acetate (9:1) to elute the product.

M.P.-109.5-110° (hexane-dichloromethane).

U.V.-224, 295 nm ($\epsilon$ 44,700; 15,900).

EXAMPLE 31

1-(3,4-Methylenedioxybenzyl)-2,3-bisphenylthioindole

This compound was prepared in the same manner as described in Example 30 except that after the addition of 3,4-methylenedioxybenzyl bromide, the reaction mixture was stirred at 90° for 3 h. The crude product was obtained as a solid.

M.P.-170°-171° (ethyl acetate-hexane).

U.V.-(dioxan) 260, 297 nm ($\epsilon$ 11,200; 15,900).

EXAMPLE 32

1-Ethyl-2,3-bis-phenylthioindole 4.37 g of 2,3-bis-phenylthionidole, 5 ml ethyl iodide, 10 ml NaOH (50% aqueous solution), 100 ml benzene and 4.37, actually Adogen 464 sold by Aldrich Chem. Co. as a phase transfer catalyst were mixed and stirred vigorously for 1 hour at room temperature. The rection mixture was poured into water, the phases separated, washed with 1:9 hydrochloric acid-water, dried over sodium sulfate, and evaporated to dryness. The residue was placed on short silica gel column and eluted with dichloromethane. This process gave the title compound as an oil.

Mass spectrum, 361 (M+).

Following the same procedure the following compound was made: 1-Methyl-2,3-bisphenylthioindole.

M.P.-103°-103.5° (dichloromethane-MeOH).

EXAMPLE 33

1-(2-Methoxycarbonylbenzyl)-2-phenylsulfinyl-3-phenyl-sulfonylindole

A solution of 86% m-chloroperbenozic acid (1.74 g) in dry dichloromethane (50 ml) was added to a stirred solution of 1-(2-methoxycarbonylbenzyl)-2,3-bisphenylthioindole (1.2 g, 0.249 mmol) in dry dichloromethane (100 ml) at 0°. At the end of 16 hours the reaction mixture was washed with saturated sodium carbonate solution, dried and evaporated in vacuo. The solid residue was crystallized from dichloromethane-ether to give the crystalline product.

M.P.-218°-219° (dichloromethane-ether).

U.V.-223, 300 nm ($\epsilon$ 33,900; 18,600).

The following compound was prepared in the same manner: 1-Methyl-2-phenylsulfinyl-3-phenylsulfonylindole;

M.P.-114°-116° (ether-dichloromethane).

EXAMPLE 34

1-(3,4-Methylenedioxybenzyl)-2-phenylsulfinyl-3-phenylsulfonylindole

This compound was prepared in the same manner as described in Example 33 except that after the addition of the m-chloroperbenzoic acid, the reaction mixture was stirred at room temperature for 4 hours.

M.P.-188°-189° (dichloromethane-ether).

U.V.-244, 299 nm ($\epsilon$ 20,900; 18,200).

EXAMPLE 35

1-Ethyl-2-phenylsulfinyl-3-phenylsulfonylindole and 1-Ethyl-2,3-bisphenylsulfonylindole 4.89 g Crude N-ethyl-2,3-bisphenylthioindole was dissolved in methylene chloride (500 ml) and treated with m-chloroperbenzoic acid (85%) (13.5 g) in portions at room temperature. The mixture was stirred at room temperature for 16 hours. The mixture was washed twice with 10% sodium carbonate solution, dried and evaporated to give 5.41 g solid. Tlc analysis (silica gel-dichloromethane) showed the presence of two compounds, neither of which were starting material. The mixture was separated by column chromatography on silica gel (240 g) using dichloromethane as the eluting solvent. 1-Ethyl-2,3-bisphenylsulfonylindole was eluted first followed by the sulfoxide 1-Ethyl-2-phenylsulfinyl-3-phenylsulfonylindole.

1-Ethyl-2-phenylsulfinyl-3-phenylsulfonylindole had the following physical constants.

M.P.-173°-173.5° (dichloromethane-ether).

1-Ethyl-2,3-bisphenylsulfonylindole had the following physical constants,

M.P.-207°-208.5° (dichloromethane-hexane),

EXAMPLE 36

1-Benzyl-2-phenylsulfinyl-3-phenylsulfonylindole 1.335 g Of crude N-benzyl-2,3-bisphenylthioindole was dissolved in methylene chloride (100 ml) and m-chloroperbenzoic acid (2.6 g) was added in portions. The mixture was stirred for 3 hours at room temperature, washed two times with saturated sodium carbonate solution, and evaporated to dryness. The resulting residue was recrystallized from dichloromethane-ether.

EXAMPLE 37

1-Benzyl-2,3-bis-phenylsulfonylindole

A mixture of 14.57 g of 2,3-bisphenylthioindole, 20 g of benzyltriethylammonium chloride, 20 g of sodium hydroxide, 20 ml water and 250 ml toluene was refluxed with vigorous stirring for 3 hours 45 min. The phases were separated after cooling and the organic phase washed with 1:9 hydrochloric acid:water, dried and evaporated. The resulting oil was dissolved in methylene chloride and percolated through a short silica gel column to remove the excess benzyltriethylammonium chloride. The resulting oil was used without further purification.

The crude material from the preceeding paragraph (17.12 g) was dissolved in methylene chloride (500 ml) and cooled in ice. Then m-chloroperbenzoic acid (85%, 43 g) was added in portions with stirring. Upon addition, the volume was adjusted to 1 L with methylene chloride to facilitate stirring and the reaction was allowed to come to room temperature. The reaction was monitored periodically by tlc silica gel dichloromethane. After stirring for 3 days, 10 g more of theoxidant was added. On the 11th day, another 10 g was added and the reaction was worked up after stirring for 12 days. The solution was washed three times with saturated sodium carbonate solution, dried and evaporated to give a white solid. This solid was slurried with ether and the solids broken up to give a uniform suspension which was filtered and washed with ether to give the title compound, homogeneous on tlc.

M.P.-205°-206° (dichloromethane-ether).
U.V.-254, 303 nm ($\epsilon$ 15,100; 2190).

Proceeding in the same manner, the following compound was prepared: 1-ethyl-2,3-bisphenylsulfonylindole M.P.-207°-208.5° (dichloromethane-ether).
I.R.-(CHCl$_3$) 17728.

EXAMPLE 37

1-Benzyl-2-(2-aminoethylamino)-3-phenylsulfonylindole dihydrochloride

A suspension of 1-benzyl-2-chloro-3-phenylsulfonylindole (1.0 g, 2.6 mmol) in ethylene diamine (10 ml) was heated at 80° for 1 hour. Water was added to the solution and the aqueous phase was decanted from the gummy material which separated after standing for 20 min. To this gum was added excess ethereal hydrogen chloride followed by dichloromethane. The gelatinous solid which formed was collected by filtration, washed with ethyl acetate and dried to give a solid. This solid was recrystallized from dichloromethane to give the title compound.

M.P.-164°-167° dec (dichloromethane).
U.V.-221, 278 sh, 287 nm ($\epsilon$ 18,200; 6170; 6170).

EXAMPLE 41

Assay for Inhibition of Lipoxygenase Activity By Human Polymorphonuclear Leukocytes

Experimental Procedures

1. Preparation of the cells: The PMNs were prepared from 200-300 ml of heparinized blood of healthy donors not receiving any medication for at least 7 days using Ficol-Hypaque gradients. In general, PMNs were greater than 90% pure and their viability was assessed by dye-exclusion to be better than 95%. The cells were suspended in phosphate buffered saline containing 1.0 mM CaCl$_2$ (PH 7.4) and 0.1% ovalbumin, and used within 30 minutes.

2. Lypoxygenase Assay: Incubations were carried out at 37° for 5 minutes in a total volume of 0.2 ml arachidonic acid 1-C$^{14}$ (1×10$^{-4}$M unless otherwise indicated, and approximately 300,000 cpm) was added to a suspension of cells (ca 5×10$^6$) to initiate the reaction. Prior to the addition of above substrate, the test substances were added to the cells at appropriate concentrations and pre-incubated at 37° for 5 minutes. In general, stock solutions of test substances were prepared in ethanol (or other appropriate solvents) and diluted with either incubation-buffer or water. The final concentration of ethanol in the incubation did not exceed 1%. Boiled enzyme blanks and controls containing no test compound were always included. The incubations were terminated by the addition of 0.6 ml of methanol, vortexed and kept on ice for 30 minutes.

1.6 ml of deionized water was added, vortexed, centrifuged, the supernatants decanted and kept in the freezer overnight. Separation of arachidonic acid and lipoxygenase products were carried out using "Baker" disposable C$^{-18}$ extraction columns (1 ml capacity). The columns were prewashed with MeOH (2.0 ml) followed by deionized water (2 ml). After most of the solvent was removed, 2.0 ml of the supernatant was applied to the extraction columns and the solvent was allowed to flow through. The columns were then washed with 5 ml of deionized water and the eluate was discarded. The columns were then eluted with 6.0 ml of a solvent mixture (acetonitrite:H$_2$O:acetic acid in the proportion 50:50:0.1) which recovers all the arachidonic acid metabolites including 5-HETE and LTB$_4$ with very little of arachidonic acid (AA) being eluted (less than 2-3% of incubated counts). The columns were then eluted with 2.0 ml of methanol (forced through by N$_2$) which elutes all of the unreacted substrate AA. The eluates were collected in scintillation vials and 1.0 ml aliquot from each of the two fractions were counted for radioactivity in a Packard liquid scintillation counter. From the radioactivity data thus obtained percent yields of total lipoxygenase products in blanks, controls and drug containing tubes were calculated as well as percent inhibition by the test compounds.

What is claimed is:

1. A compound of the formula:

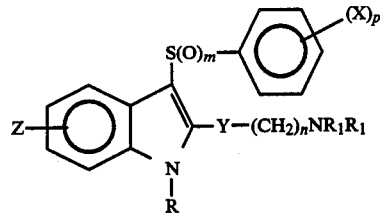

wherein

R is alkyl of 1 to 8 carbon atoms, benzyl or benzyl substituted with one or more groups independently selected from the group consisting of alkyl of 1 to 4 carbon atoms, halo, hydroxy, —OR$_2$ where R$_2$ is alkyl of 1 to 4 carbon atoms, —OCF$_3$, —SO$_2$CH$_3$, —CO$_2$H, —CO$_2$R$_2$, —CHO, —NO$_2$, —CF$_3$, —SCN, and —OCH₂O— attached at adjacent carbon atoms, which is methylenedioxy;
R₁ is hydrogen or alkyl of 1 to 4 carbon atoms;
Y is S, NH, or NR₂;
n is 2, 3, 4, 5, 6, 7, or 8;
m is 0, 1 or 2;
X and Z are independently alkyl of 1 to 4 carbon atoms, halo, hydroxy, —OR₂ where R₂ is alkyl of 1 to 4 carbon atoms, —OCF₃, —SO₂CH₃, —CO₂H, —CO₂R₂, —CHO, —NO₂, —CF₃ or —SCN;
p is 0, 1, 2, 3, 4, or 5; or a pharmaceutically acceptable salt thereof.

2. A compound according to claim 1 wherein Y is S.

3. A compound of claim 2 wherein n is 2, m is 2 and Z is hydrogen.

4. A compound according to claim 3 wherein R is benzyl or substituted benzyl.

5. A compound according to claim 4 which is 1-benzyl-2-aminoethylthio-3-phenylsulfonylindole or an acid addition salt thereof.

6. A compound according to claim 4 which is 1-(2-methoxycarbonylbenzyl)-2-aminoethylthio-3-phenylsulfonylindole or an acid addition salt thereof.

7. A compound according to claim 4 which is 1-(4-chlorobenzyl)-2-aminoethylthio-3-phenylsulfonylindole or a pharmaceutically acceptable acid addition salt thereof.

8. A compound according to claim 4 which is 1-(-4-methylbenzyl)-2-aminoethylthio-3-phenylsulfonylindole or a pharmaceutically acceptable acid addition salt thereof.

9. A compound according to claim 4 which is 1-benzyl-2-aminoethylthio-3-(4-methylphenylsulfonyl)indole or a pharmaceutically acceptable acid addition salt thereof.

10. A compound according to claim 4 which is 1-benzyl-2-aminoethylthio-3-(4-chlorophenylsulfonyl)indole or a pharmaceutically acceptable acid addition salt thereof.

11. A method for treating inflammation, which method comprises administering either alone or in admixture with a pharmaceutically acceptable excipient, a compound of the formula

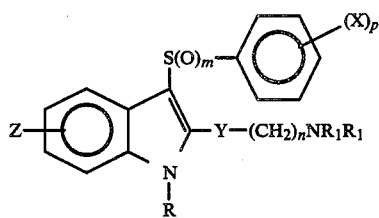

wherein
R is alkyl of 1 to 8 carbon atoms, benzyl or benzyl substituted with one or more groups independently selected from the group consisting of alkyl of 1 to 4 carbon atoms, halo, hydroxy, —OR₂ where R₂ is alkyl of 1 to 4 carbon atoms, —OCF₃, —SO₂, CH₃, —CO₂H, —CO₂R₂, —CHO, —NO₂, —CF₃, —SCN and —OCH₂O— attached at adjacent carbon atoms, which is methylenedioxy;
R₁ is independently hydrogen or alkyl of 1 to 4 carbon atoms;
Y is SO, NH, or NR₂;
n is 2, 3, 4, 5, 6, 7, 8;
m is 0, 1 or 2;
X and Z are independently alkyl of 1 to 4 carbon atoms, halo, hydroxy, —OR₂ where R₂ is alkyl of 1 to 4 carbon atoms, —OCF₃, —SO₂CH₃, —CO₂H, —CO₂R₂, —CHO, —NO₂, —CF₃ or —SCN;
p is 0, 1, 2, 3, 4 or 5; or a pharmaceutically acceptable salt thereof.

12. The method of claim 11 wherein Y is S.

13. The method of claim 11 wherein n is 2, m is 2 and Z is hydrogen.

14. The method of claim 11 wherein R is benzyl or substituted benzyl.

15. The method of claim 11 in which the compound to be administered is 1-(2-methoxycarbonylbenzyl)-2-aminoethylthio-3-phenylsulfonylindole or an acid addition salt thereof.

16. The method of claim 11 in which the compound to be administered is 1-(4-chlorobenzyl)-2-aminoethylthio-3-phenylsulfonylindole or a pharmaceutically acceptable acid addition salt thereof.

17. The method of claim 11 in which the compound to be administered is 1-(-4-methylbenzyl)-2-aminoethylthio-3-phenylsulfonylindole or a pharmaceutically acceptable acid addition salt thereof.

18. The method of claim 11 in which the compound to be administered is 1-benzyl-2-aminoethylthio-3-(4-methylphenylsulfonyl)indole or a pharmaceutically acceptable acid addition salt thereof.

19. A compound of the formula:

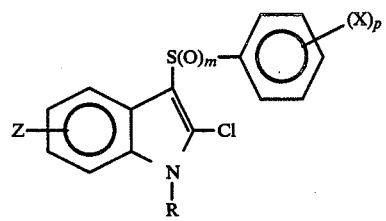

wherein
R is alkyl of 1 to 8 carbon atoms, benzyl or benzyl substituted with one or more groups independently selected from the group consisting of alkyl of 1 to 4 carbon atoms, halo, hydroxy, —OR₂ where R₂ is alkyl of 1 to 4 carbon atoms, —OCF₃, —SO₂CH₃, —CO₂H, —CO₂R₂, —CHO, —NO₂, —CF₃, —SCN, and —OCH₂O— attached at adjacent carbon atoms, which is methylenedioxy;
R₁ is hydrogen or alkyl of 1 to 4 carbon atoms
m is 0, 1 or 2;
X and Z are independently alkyl of 1 to 4 carbon atoms, halo, hydroxy, —OR₂ where R₂ is alkyl of 1 to 4 carbon atoms, —OCF₃, —SO₂CH₃, —CO₂H, —CO₂R₂, —CHO, —NO₂, —CF₃ or —SCN;
p is 0, 1, 2, 3, 4, or 5.

20. A compound according to claim 19 which is 1-benzyl-2-chloro-3-phenylsulfosulfonylindole.

21. A compound according to claim 19 which is 1-benzyl-2-chloro-3-(4-methylphenylsulfonyl)indole.

22. A compound according to claim 19 which is 1-benzyl-2-chloro-3-(4-chlorphenylsulfonyl)indole.

23. A compound according to claim 19 which is 1-(4-chlorobenzyl)-2-chloro-3-phenylsulfonylindole.

24. A compound according to claim 19 which is 1-(2-methylcarbonylbenzyl)-2-chloro-3-phenylsulfonylindole.

25. A compound according to claim 19 which is 1-(4-methylbenzyl)-2-chloro-3-phenylsulfonylindole.

26. The method of claim 11 in which the compound to be administered is 1-benzyl-2-aminoethylthio-3-(4-chlorophenylsulfonyl)indole or a pharmaceutically acceptable acid addition salt thereof.

* * * * *